United States Patent [19]

Mochida et al.

[11] Patent Number: 5,154,896
[45] Date of Patent: Oct. 13, 1992

[54] APPARATUS FOR PROMOTING REACTION BETWEEN SOLID AND LIQUID PHASES

[75] Inventors: Ei Mochida; Kenji Usui, both of Tokyo, Japan

[73] Assignee: Mochida Pharmaceutical Co., Ltd., Tokyo, Japan

[21] Appl. No.: 577,538

[22] Filed: Sep. 5, 1990

[30] Foreign Application Priority Data

Sep. 5, 1989 [JP] Japan ............................. 1-229700

[51] Int. Cl.$^5$ ............................................. B01J 8/06
[52] U.S. Cl. ................................... 422/209; 422/63; 422/64; 422/72; 436/45; 436/50; 494/16
[58] Field of Search ............... 422/209, 229, 72, 64, 422/63, 270; 436/45, 48, 50; 494/16, 20; 366/214

[56] References Cited

U.S. PATENT DOCUMENTS

| | | | |
|---|---|---|---|
| 3,115,966 | 12/1963 | Leiter | 198/346.2 |
| 3,163,404 | 12/1964 | Kraft et al. | 494/16 |
| 3,304,990 | 2/1967 | Ontko et al. | 494/16 |
| 3,882,716 | 5/1975 | Beiman | 422/72 |
| 3,909,201 | 9/1975 | Matte | 422/72 |
| 3,980,227 | 9/1976 | Witty et al. | 494/7 |
| 4,208,484 | 6/1980 | Sogi et al. | 422/72 |
| 4,479,720 | 10/1984 | Mochida et al. | 366/214 |
| 4,482,636 | 11/1984 | Mochida et al. | 422/72 |
| 4,797,258 | 1/1989 | Mochida | 422/65 |
| 4,834,944 | 5/1989 | Wakatake | 422/64 |
| 4,960,566 | 10/1990 | Mochida | 422/65 |

FOREIGN PATENT DOCUMENTS

| | | | |
|---|---|---|---|
| 352689 | 1/1990 | European Pat. Off. | 422/72 |
| 58-61469 | 4/1983 | Japan . | |
| 61-114731 | 6/1986 | Japan . | |
| 61-114732 | 6/1986 | Japan . | |
| 61-61857 | 12/1986 | Japan . | |

Primary Examiner—Robert J. Warden
Assistant Examiner—Krisanne Thornton
Attorney, Agent, or Firm—Burns, Doane, Swecker & Mathis

[57] ABSTRACT

An apparatus for reaction between a solid phase and a liquid phase of the present invention allows a tubular reaction vessel accommodating the liquid phase that reacts with the solid phase bound to the inside surface of said reaction vessel to hold in the peripheral region of a rotating element inclined with respect to the horizontal direction and also allows said tubular reaction vessel to repeat a predetermined number of cycles, each consisting at least of the steps of rotating continuously said rotating element in the inclined state at a predetermined constant speed for a predetermined time and loading/unloading said reaction vessel for the rest time of the rotating element. Because of these features, the apparatus of the present invention makes possible to have a simple construction which can be easily handled and can continuously promote the reaction in a plurality of the reaction vessels under identical reaction conditions for identical reaction time at a series of time.

12 Claims, 12 Drawing Sheets

No.40

APPARATUS FOR PROMOTING REACTION BETWEEN SOLID AND LIQUID PHASES

BACKGROUND OF THE INVENTION

1. Field of the Invention

This invention relates to an apparatus for promoting a reaction between solid and liquid phases. The apparatus is used to insure that an efficient reaction takes place between a solid-phase reactive substance that is bound to the inside surface of a tubular reaction vessel and a reactive substance that exists in the liquid phase in the reaction vessel. More particularly, this invention relates to an apparatus for promoting a reaction between solid and liquid phases that is suitable for use in promoting various reactions including immunoreactions, enzymatic reactions and reactions using DNA probes.

2. Description of the Prior Art

Immunoassay techniques utilizing such reactions as antigen-antibody reactions are currently employed as a means of measuring concentration of substances that are present in very small amounts in body fluids such as urine, blood serum, blood plasma and the like, and concentration of drugs administered to a living body in the body fluids.

These reactions can conveniently be carried out by using the inside surface of reaction vessels as a carrier for immobilizing and insolubilizing antibodies, antigens and other reactive substances. For example, plastic test tubes are easy to handle and used with preference since they serve both as a carrier for immobilizing a reactive substance and as a reaction vessel. Reactions in vessels having a reactive substance immobilized or insolubilized on their inner wall are conventionally carried out by a stationary process in which the reaction vessel such as a test tube is allowed to stand in an upright position for the reaction to take place therein. However, in this stationary process, the area of the inside surface (the inner wall) of the reaction vessel that can be utilized for the reaction is limited by the volume of the sample solution in the vessel and the amount of the aforementioned reactive substance that can be bound to said inside surface is also limited by the available surface area. Thus, the amount of the aforementioned reactive substance relative to the sample solution cannot be increased as much as other conventional carriers used in the stationary method such as plastic beads, filter paper and fine cellulosic particles and this had led to an unduly prolonged reaction time.

With a view to overcoming these disadvantages, the applicant of the present invention has already proposed an apparatus capable of permitting the intended reaction to be fully carried out within a short period of time by an inclined rotational method wherein the reaction vessel is rotated with its own longitudinal axis inclined at a predetermined angle from horizontal direction. Japanese Patent Publication Kokoku No. 61-61857 discloses a process wherein the inclined reaction vessel is simultaneously rotated around its own longitudinal axis with the axis inclined at a predetermined angle from the horizontal direction and transported in horizontal direction to automatically control the reaction time, as well as an apparatus used for carrying out said process. Japanese Patent Application Kokai No. 58-61469 discloses an apparatus wherein the inclined reaction vessel is not only rotated around its own longitudinal axis but also revolved around another axis parallel to the longitudinal axis of the reaction vessel to achieve transporting and automatically control the reaction time. The key concept of these apparatuses is that if an inclined reaction vessel is allowed to rotate about its own axis, the liquid phase in the vessel is moved in contact with a wide area of its inside surface to promote the reaction taking place within the vessel, and the intended effect can be attained by this approach.

Further, the reaction apparatuses described in the aforementioned prior patents are so designed that the reaction vessel is to be loaded manually on the apparatus and no teaching whatsoever is made of an apparatus in which the reaction vessel can be automatically loaded.

Under these circumstances, this applicant proposed in Japanese Patent Application Kokai Nos. 61-114731 and 61-114732 an apparatus in which the aforementioned reaction vessel is raised from an inclined position in which it is allowed to rotate about its own axis to an upright position. This erecting apparatus serves to hold the reaction vessel in an upright position so that in various immunoassay procedures, particularly in reaction procedures, a step such as washing that precedes or follows the step in which the reaction vessel is rotated in an inclined state in order to promote the reaction can be performed in an easy and advantageous manner.

The above-described apparatuses proposed by the applicant for carrying out the reaction between a solid and a liquid phase are capable of achieving the intended promotion of the reaction of interest. However, each of the reaction vessels employed has to be rotated about its own axis and this increases not only the structural complexity but also the cost of the reaction apparatus. Further, the procedures involved in loading and unloading the individual reaction vessels from the apparatus are extremely cumbersome and complicated.

The reaction apparatus proposed in Japanese Patent Publication Kokoku No. 61-61857, supra, creates the force of rotating the reaction vessels by the friction between the holder or belt and each reaction vessel. This is also true with the reaction apparatus proposed in Japanese Patent Application KOKAI No. 58-61469, supra which creates the force of rotating the vessel supporting holder by the friction between said vessel supporting holder and the rotating disk which is driven by a motor. Accordingly, if the outside surface (the outer wall) of a certain reaction vessel is wetted accidentally with the liquid content or water, or if the environment of use is such that the moisture in the surrounding atmosphere condenses to collect on said outside surface of that reaction vessel, there occurs an abrupt drop in the effective frictional force and the failure to achieve the necessary rotation during the predetermined reaction time can lead to inexact measurements. Thus, it has been difficult in the case of power transmission with friction to insure that no slippage will occur under any conditions. On the other hand, the reaction conditions must be made uniform in measurements, particularly in immunoassays which make use of immunological reactions, and yet prior art reaction apparatuses described above will often fail to insure completely identical reaction conditions (especially, agitating or mixing conditions, the rotational speed and the number of rotations of each reaction vessel) in all reaction vessels (spinning conditions).

In addition, the procedures involved in loading and unloading the individual reaction vessels from the apparatus have been extremely cumbersome and complicated.

Further, in order to insure identical conditions of the reaction that takes place in many reaction vessels and to enable even unskilled operators to achieve the intended measurement under the same conditions, the reaction apparatus is preferably designed in such a way that the individual reaction vessels can be loaded and unloaded automatically to realize automated measurements. However, none of the existing reaction apparatuses are adapted to permit the reaction vessels to be loaded and unloaded in a simple and automatic way. The erecting apparatuses described in Japanese Patent Application KOKAI Nos. 61-114731 and 61-114732, supra, are not designed so that the reaction vessels are loaded in their associated loading positions in a pinched state and, as a result, the force exerted upon the reaction vessels during their loading is not uniform enough to insure smooth loading and this can cause either spillage of the liquid content or accidental breaking of the vessels. The failure to load or unload reaction vessels in a safe, correct and reliable manner has been particularly common in such cases as where vessel securing means are employed.

BRIEF SUMMARY OF THE INVENTION

A first objective, therefore, of the present invention is to solve the aforementioned problems of the prior art and to provide an apparatus for reaction between solid and liquid phases having a simple structure which is capable of promoting a reaction between a solid phase-reactive substance immobilized on an inside surface of a reaction vessel and a liquid phase-reactive substance contained in a tubular reaction vessel having an open end as effective as conventional apparatus, by means of holding the reaction in the peripheral region of a rotating element inclined at a predetermined angle with respect to the horizontal direction the reaction vessel and allowing said rotating element to rotate in the inclined state, and which is capable of providing identical reaction conditions for a plurality of reaction vessels even for those not skilled in the art.

A second objective of the present invention is to provide an apparatus for the reaction between solid and liquid phases which has not only realized the above-mentioned first objective but also is capable of loading and unloading a tubular reaction vessel in associated loading positions without breaking or spillage of the liquid content but in a safe, correct, reliable and smooth way, with the vessel being held in, for example, a vertical position; said apparatus being of simple construction with easy operation so that even unskilled operators can easily handle a plurality of the reaction vessels.

In order to attain the objectives described above, the present inventors made extensive studies on a reaction apparatus of a simple construction in which the reaction between a solid-phase reactive substance bound to the inside surface of more than one tubular reaction vessel and the liquid phase accommodated in each of said reaction vessels could be promoted in a uniform and efficient way within all reaction vessels. As a result, it was found that when a rotating element having a plurality of said reaction vessels held to its peripheral region was allowed to rotate about its own longitudinal axis, with it being inclined at a predetermined angle with respect to the horizontal direction so that the individual vessels would be rotated in an inclined state, each of them made one rotation about its own axis in the direction of gravity while the rotating element revolved fully once, whereby the sample solution in each reaction vessel could be allowed to move around the inside surface to attain maximum contact of the surface area. The present invention has been accomplished on the basis of this finding.

According to a first aspect of the present invention, there is provided an apparatus for carrying out a reaction between a solid phase and a liquid phase that comprises:

a rotating element which is rotatable, with it being inclined at a predetermined angle with respect to the horizontal direction, around a central shaft perpendicular to said inclination;

a rotational drive means which causes said rotating element to rotate around said central shaft, with said drive means being inclined; and a holding means for holding in its peripheral region of said rotating element a tubular reaction vessel having an open end and accommodating the liquid phase that reacts with the solid phase bound to the inside surface of said reaction vessel, which apparatus is further characterized by repeating a predetermined number of cycles each consisting at least of the steps of allowing said rotating element to rest for a predetermined time, allowing said element to rotate in the inclined state at a predetermined constant speed for a predetermined time and then bringing said element to a stop following rotation by a predetermined angle.

According to a second aspect of the present invention, there is provided an apparatus for carrying out a reaction between a solid phase and a liquid phase that comprises:

a rotating element which is provided in its peripheral region with a plurality of holding means for holding a tubular reaction vessel having an open end and accommodating the liquid phase that reacts with the solid phase bound to the inside surface of said reaction vessel, said rotating element having a central shaft that crosses said holding means at a right angle and being rotatable around said central shaft;

a rotational drive means which causes said rotating element to rotate around said central shaft;

a tilting means which causes said rotating element to be inclined at a predetermined angle with respect to the horizontal direction; and a control means for controlling said drive means and said tilting means in such a way that a predetermined number of cycles each consisting of the steps of allowing said rotating element to rest in a horizontal position for a predetermined time, tilting the element by a predetermined angle, allowing the element to rotate in the tilting state at a predetermined constant speed for a predetermined time, bringing the element back to the horizontal position, allowing the element to rest for a predetermined time, and finally allowing the element to rotate in said horizontal position by a predetermined angle.

In a preferred embodiment of the second aspect of the present invention, said rotating element comprises a top disk, one or more intermediate disks and a bottom disk that are secured to one another with them being spaced by predetermined distances in the direction parallel to said central shaft which is secured to at least one of said disks, said holding means being composed of a predetermined number of holes into which said reaction vessel can be inserted and said bottom disk which supports the bottom of said reaction vessel, said holes being formed through the peripheral region of said top disk and all of said intermediate disks in such a way that every two adjacent holes are equidistant and aligned in a way concentric with and parallel to said control shaft.

In another preferred embodiment of the second aspect, said tilting means comprises a support member for rotatably supporting said central shaft, a pivotal shaft that is secured to said support member and which crosses said central shaft at a right angle, and a pivoting means which causes said rotating element to tilt by pivoting said pivotal shaft by said predetermined angle.

In still another preferred embodiment of the second aspect, said pivoting means comprises a first rotational drive source and a first transmission means.

In yet another preferred embodiment of the second aspect, said first transmission means comprises a toothed pulley mounted on said pivotal shaft, another toothed pulley mounted on the drive shaft coupled to said first rotational drive source, and a toothed belt stretched between said toothed pulleys.

In a further preferred embodiment of the second aspect, said rotational drive means comprises a second rotational drive source and a second transmission means.

In a still further preferred embodiment of the second aspect, said second transmission means comprises a bevel gear mounted on said central shaft and another bevel gear that meshes with said first bevel gear and which is mounted on the drive shaft coupled to said second rotational drive source.

In a yet further preferred embodiment of the second aspect, said support member is composed of a rectangular frame unit, said central shaft being supported by two parallel frame members of said frame unit, said pivotal shaft being secured to one frame member which is vertical to said parallel frame members, said rotational drive means comprising a second rotational drive source coupled to a drive shaft which rotatably supports the other frame member which is vertical to said parallel frame members, a bevel gear that is mounted on said central shaft within said frame unit, and another bevel gear that meshes with said first bevel gear and which is mounted on the drive shaft coupled to said second drive source.

In a preferred embodiment of each aspect of the present invention, said predetermined angle of inclination is in the range of from 60 to 85 degrees.

Another preferred embodiment of each aspect satisfies the relationship $r\omega^2\sin\theta < g$, where r is the radius of said rotating element, $\omega$ is the angular velocity of its rotation, $\theta$ is said angle of inclination, and g is the acceleration of gravity.

In still another preferred embodiment of each aspect, said rotating element is accommodated within a thermostatic chamber or incubator.

DETAILED DESCRIPTION OF THE INVENTION

The apparatus of the present invention for promoting the reaction between a solid and a liquid phase is described below in detail with reference to the preferred embodiments shown in the accompanying drawings.

Figure 1:
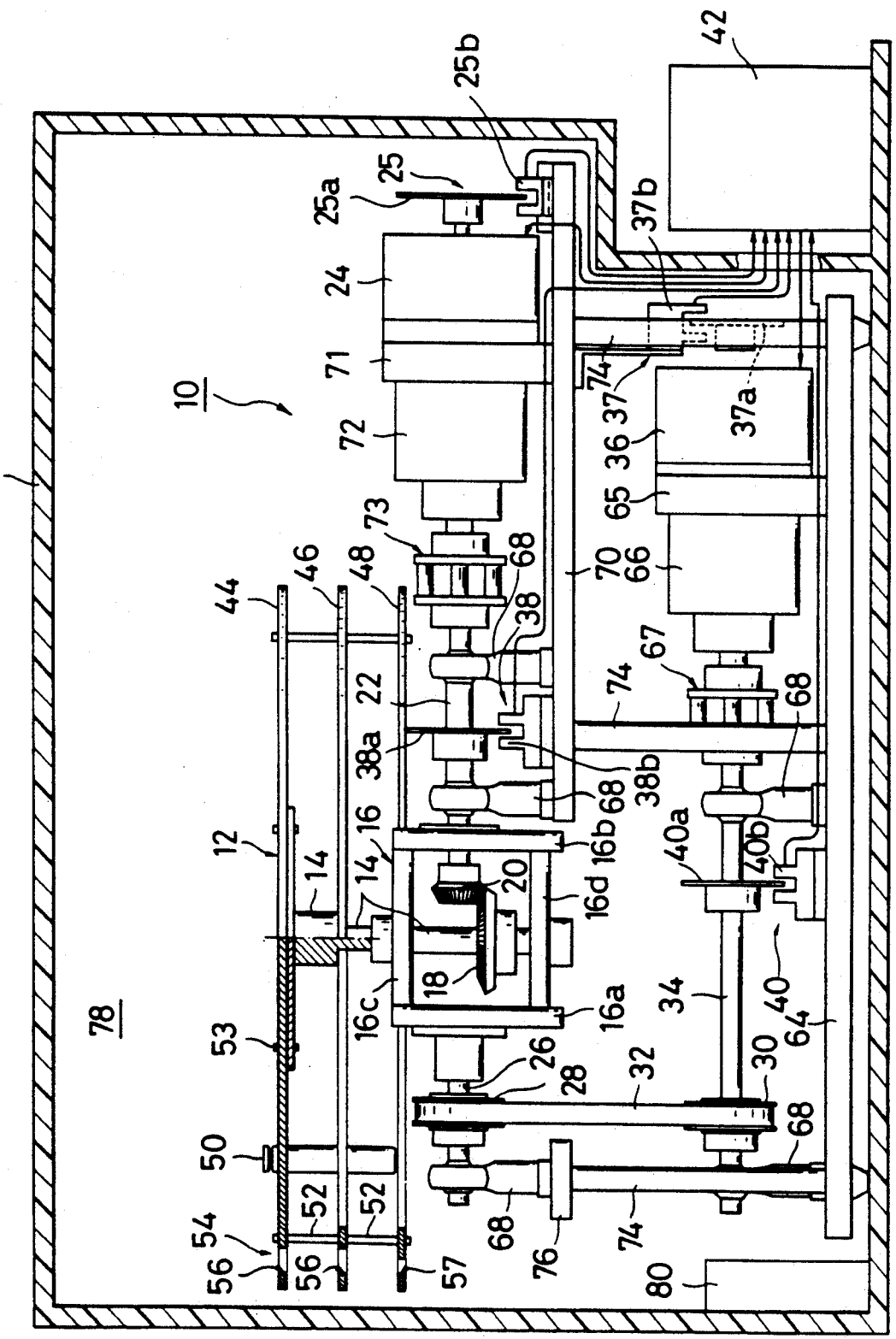
FIG. 1 is a front view showing, in partial cross section, an example of the apparatus of the present invention for carrying out the reaction between a solid and a liquid phase.
Figure 2:
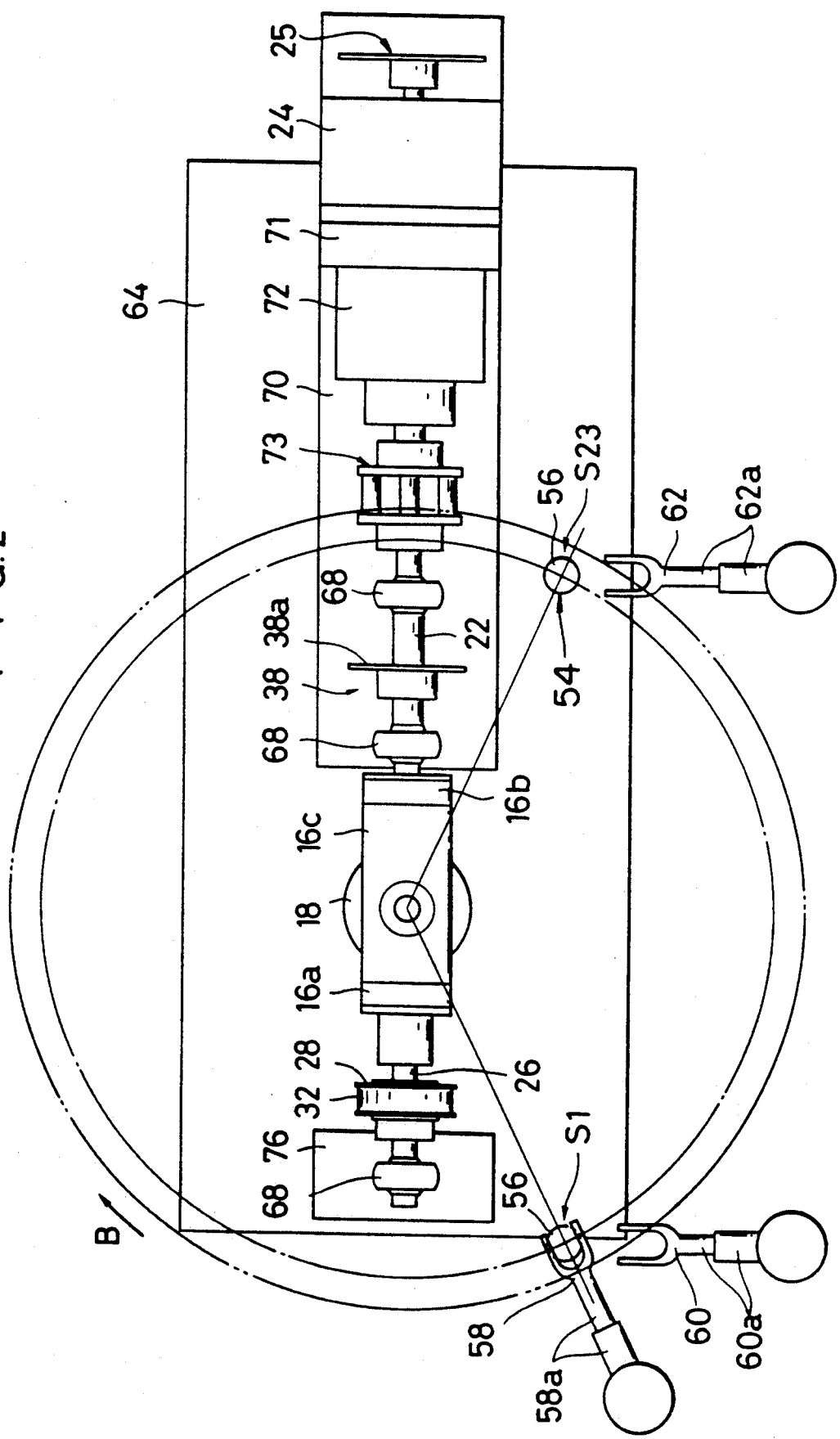
FIG. 2 is a top view, with part cut away, of the reaction apparatus shown in FIG. 1.
Figure 3:
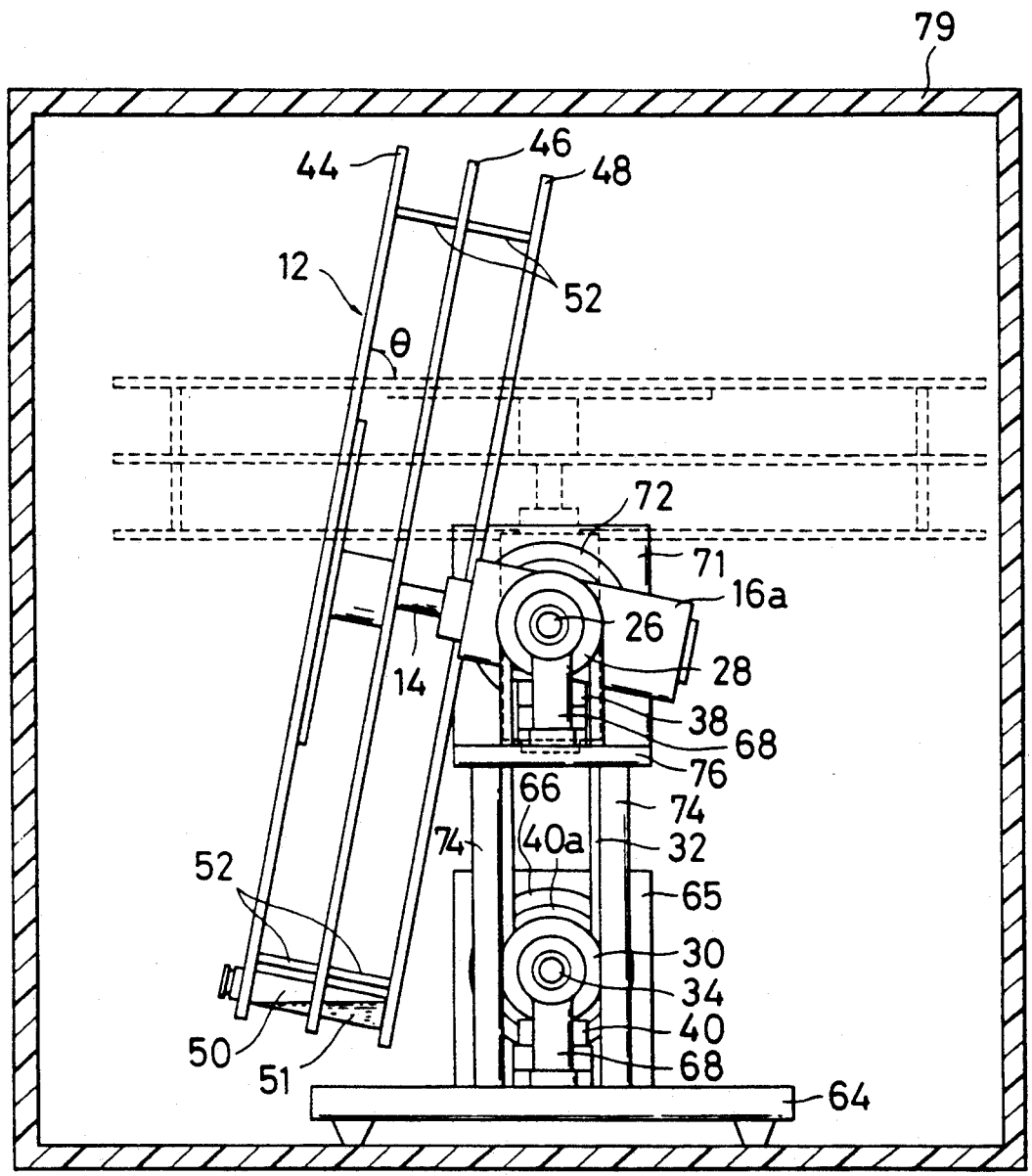
FIG. 3 is a side view of the reaction apparatus shown in FIG. 1.

FIG. 1 is a front view showing, in partial cross section, an embodiment of the apparatus of the present invention for promoting the reaction between a solid and a liquid phase in its first and second aspects; FIG. 2 is a top view of the same apparatus, with part cut away; and FIG. 3 is a side view of the same apparatus.

As shown in these drawings, the apparatus of the present invention for promoting the reaction between a solid and a liquid phase (which is hereinafter referred to simply as the "reaction apparatus") is generally indicated by 10 and comprises a rotating element 12, its central shaft 14, a rectangular frame unit 16 for rotatably supporting said central shaft 14, a bevel gear 18 mounted on the central shaft 14 in the frame unit 16, another bevel gear 20 that meshes with the bevel gear 18, a drive shaft 22 on which the bevel gear 20 is mounted, a motor 24 for rotatively driving the drive shaft 22, a pivotal shaft 26 that is secured to a frame member 16a parallel to the central shaft 14 of the frame unit 16 and which has a central axis common to the drive shaft 22, a toothed pulley 28 mounted on the pivotal shaft 26, another toothed pulley 30, a toothed belt 32 stretched between these two pulleys 28 and 30, a drive shaft 34 on which the toothed pulley 30 is mounted, a motor 36 for rotatively driving the drive shaft 34, a sensor 38 that is mounted on the drive shaft 22 to detect the position in which the rotating element 12 is brought to a stop in its horizontal state, a sensor 40 that is mounted on the drive shaft 34 to detect whether the rotating element 12 is in its horizontal or inclined position, sensors 25 and 37 that are mounted on the motors 24 and 36, respectively to detect the position of the rotating element 12, and a control unit 42 that controls the rotational driving of the motors 24 and 36 in response to the detection signals from the sensors 25, 37, 38 and 40.

The rotating element 12 is composed of three disks 44, 46 and 48 that are spaced parallel to one another and secured together by means of stays 52, with the spacing between adjacent disks being properly determined by the length of a reaction vessel 50. In the example shown, each of the intermediate disk 46 and the bottom disk 48 is an annular plate having the central circular hole through which the central shaft 14 can penetrate. The top disk 44 has the central shaft 14 secured vertically to its center by means of four bolts 53. The three disk 44, 46 and 48 are preferably equal in diameter but this is not necessarily the case and they may have different diameters. The spacing between adjacent disks 44 and 46 is preferably equal to that between disks 46 and 48 but this is not necessarily the case and the two spacings may differ from each other.

The rotating element 12 must be subjected to a number of steps such as tilting from a horizontal position, rotation in an inclined state at constant speed and returning to the horizontal position within a short period of time, and to meet this need, said rotating element 12 is preferably as lightweight as possible. Accordingly, the three disks 44, 46 and 48 of which the rotating element 12 is composed, in particular, the two upper disks 44 and 46, are preferably as thin as possible to insure weight reduction. The bottom disk 48 is also preferably as thin as possible on the condition that it has a sufficient strength to support the reaction vessel 50 from below. In the example shown, the intermediated disk 46 is a single disk but this is not necessarily the case and said disk may be composed of more than one disk.

Figure 4A:
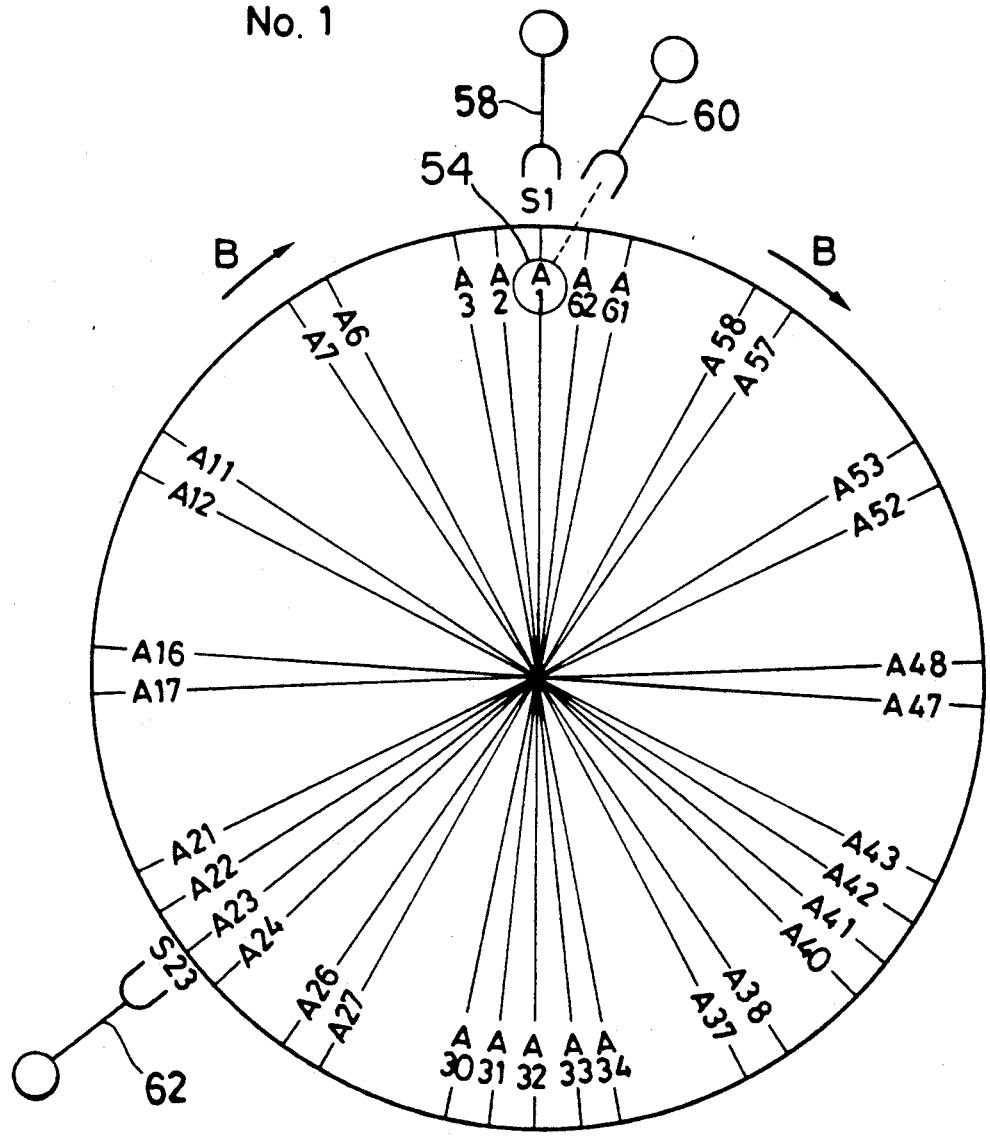
FIGS. 4a to 4f illustrate the sequence of operations of the reaction apparatus shown in FIG. 1.
Figure 4B:
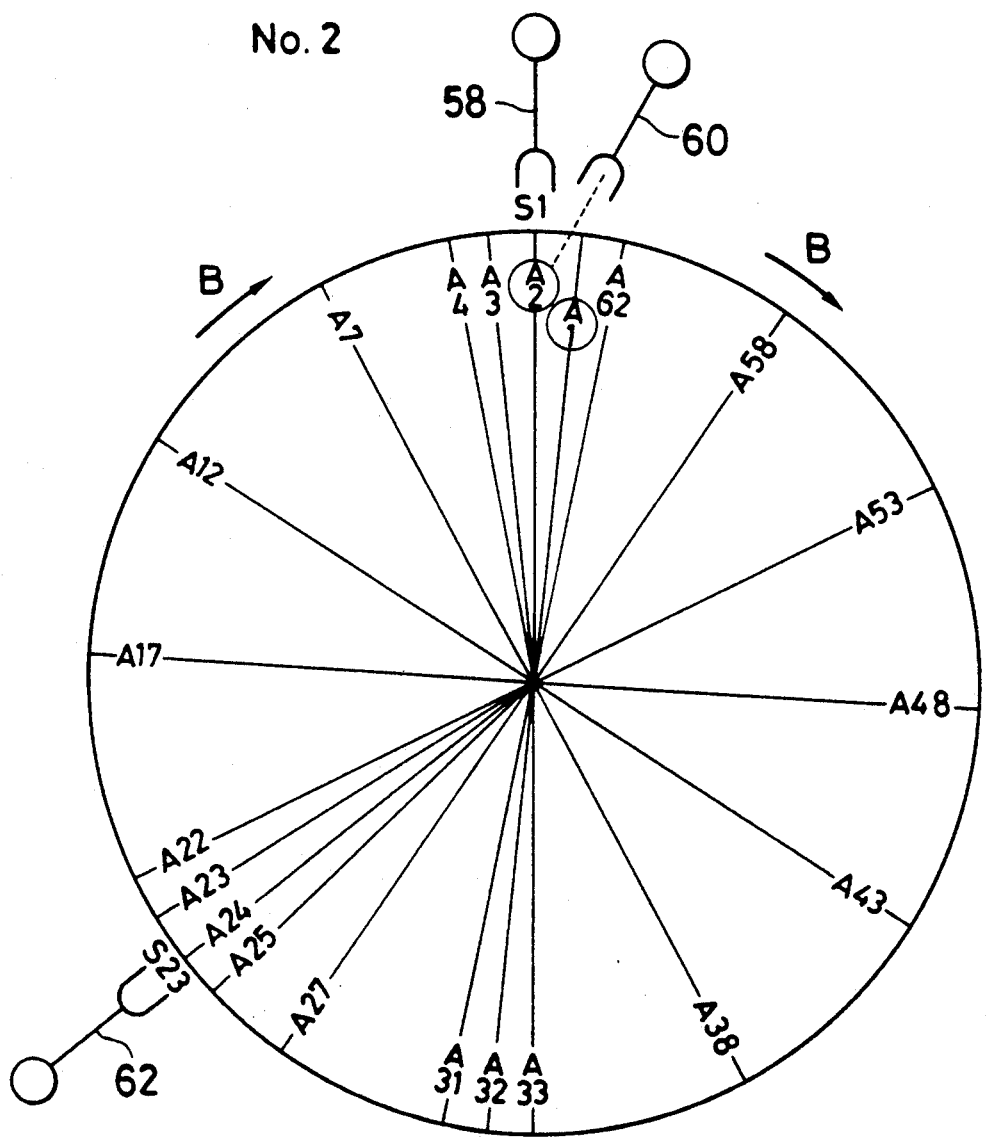

The rotating element 12 has in its peripheral region a holding means 54 for holding a plurality of reaction vessels 50 equidistantly in a manner concentric with and parallel to the central shaft 14. As shown in FIGS. 2 and 4a, the holding means 54 is an assembly of seats in which the reaction vessels can be accommodated and consists of a plurality of through holes 56 that are formed equidistantly and in a concentric pattern in the top disk 44 and the intermediate disk 46 in such a way that they can accommodate the reaction vessels 50 (in the example shown, sixty-two holes 56 are formed in one disk), as well as the bottom disk 48 which supports the bottoms of the reaction vessels 50. The holding means 54 to be used in the present invention must have such a construction that when the rotating element 12 is in a horizontal position, it is capable of properly receiving the reaction vessels 50 being set from above while maintaining them in correct positions after they are received. To this end, the holes 56 to be formed in each of the disks 44 and 46 preferably have a slightly larger diameter than each reaction vessel 50, with its upper part being shaped like funnel.

In order to facilitate the removal of the reaction vessels 50, particularly to insure that pinchers 58, 60 and 62 shown in FIG. 2 can readily pinch individual reaction vessels 50, the bottom disk 48 is preferably provided with holes 57 that are smaller in diameter than the reaction vessels 50 and which serve to assist in pushing up of the reaction vessel 50 from its bottom.

Consider here the case where the reaction apparatus 10 is to be used in performing an enzyme immunoassay utilizing an antigen-antibody reaction, wherein the result of the antigen-antibody reaction is detected by an enzymatic reaction wherein a color is developed. As already mentioned, there are 62 seats for accommodating the reaction vessels 50. When the rotating element 12 is in its horizontal position, position S1 in the lower left portion of FIG. 2 may be designated as a station where a reaction vessel 50 containing a sample solution 51 which is subjected to the reaction is set, and where the reaction vessel wherein a color has developed through the reaction is removed. Further, position S23 in the lower right portion of FIG. 2 which is away in counterclockwise from station S1 by 127.74 degrees, which correspond to 22 reaction vessels, may be designated as a station where the reaction vessel 50 wherein the reaction has been promoted for a predetermined time is removed, and wherein the reaction vessel which has been washed and to which a substrate for the enzyme reaction has been added is reset.

In this case, as will be described below, 40 pitches (40 cycles) from station S1 to S23 in the direction indicated by arrow B are used for the antigen-antibody reaction, and the subsequent 22 pitches (21 cycles) from station S23 to S1 in the direction indicated by arrow B are used for the enzymatic reaction wherein a color is developed.

The pinchers 58 and 60 are provided at station S1 to load and unload the reaction vessels whereas the pincher 62 is provided at station S23. The pinchers 58, 60 and 62 are mounted to the respective arms 58a, 60a and 62a, and are capable of moving not only forward and backward in the horizontal plane but also moving up and down in the vertical plane (movable in the X-Z direction). At either station S1 or S23, these pinchers are capable of setting the reaction vessel 50 in the holding means 54 provided in the rotating element 12. Further, they are used to wash the reaction vessel 50 or transfer the reaction vessel 50 to another step after it is removed from the rotating element 12 subsequent to the completion of the intended reaction in that vessel.

In this case, the pinchers 58, 60 and 62 may be mounted on one plate (not shown) for the purpose of simple construction, and the pinchers 58, 60 and 62 are moved in X direction by means of a horizontal movement of this plate. It is to be understood, however, that the pinchers may be moved independently by using independent mechanisms.

As shown in FIGS. 1 and 3, each reaction vessel 50 is in a tubular, say, cylindrical form with only its upper end being open, and its neck portion is so constricted as to engage the pincher 58, 60 or 62 of FIG. 2. A solid-phase reactive substance such as an antibody is bound or immobilized to the inside surface of each reaction vessel 50 and a sample solution 51 (liquid phase) is placed within that reaction vessel 50.

The central shaft 14 is rotatably supported by frame members 16c and 16d on opposite sides of the frame unit 16 which constitutes a gear box for accommodating bevel gears 18 and 20, with bevel gear 18 being secured to the central shaft 14. The bevel gear 20 which meshes with the bevel gear 18 is secured to an end of the drive shaft 22 which in turn is rotatably supported on the frame member 16b of the frame unit 16. The drive shaft 22 is joint-coupled to the motor 24.

Accordingly, the rotational drive means which rotatively drives the rotating element 12 is composed of the motor 24 serving as a second rotational drive source, the associated drive shaft 22 and the bevel gears 18 and 20 which serve as a second transmission means.

The assembly of bevel gears 18 and 20 not only serves to change the rotational direction, for example by 90 degrees, but also serve a reduction gear. The diameter of the bevel gear 18 is larger than that of the bevel gear 20, and the gear ratio is typically 2. When the sensor 38 detects the rotation of the drive shaft 22, the assembly of bevel gears 18 and 20 may accordingly reduce the rotational speed to accurately control the rotation of the rotating element 12.

It is necessary that the rotating element 12 be allowed to rotate continuously about the central shaft 14 in its inclined state (see FIG. 3) for a predetermined time at a constant speed by rotating the motor 24 which serves as the drive source. It is also necessary that after completion of the rotation, the rotating element 12 stop in the position that is completely the same as the position where the rotation started. Namely, the seat where a particular reaction vessel 50 is inserted should be in the same position after the rotation of the element 12. Further, the rotating element 12, when it is in its horizontal position, must be allowed to accurately rotate by a predetermined angle, say, 5.81 degrees if there are 62 seats for the reaction vessels 50.

Hence, the motor 24 which is used as the second rotational drive source in the present invention is preferably a high-precision stepping motor which satisfies the requirement that both the rotational speed and angle be accurately controlled. Other useful motors include AC and DC servo motor, and ultrasonic motor.

The rotational speed of the motor 24 is not limited to any particular value and may be, for example, 30 rpm or 60 rpm so long as the conditions determined by the centrifugal force as will be described below are satisfied. If the rotation of the motor 24 is too slow, the reaction rate will become undesirably low. On the other hand, if the rotation of the motor 24 is too fast, the centrifugal force will retard the movement of the sample solution 51 in the reaction vessel 50, which also results in an undesirably low reaction rate. The period for which the rotating element 12 is allowed to rotate continuously also is not limited to any particular value and may be properly selected in accordance with the type of the antigen-antibody reaction to be promoted between the sample solution in a reaction vessel 50 and the solid phase immobilized to the inside surface of the reaction vessel 50. In the apparatus shown in the drawings, the rotating element 12 is designed to rotate continuously for 25 seconds.

The assembly of bevel gears 18 and 20 constitutes the second transmission means to be used in the present invention and may be composed of straight bevel gears, spiral bevel gears, hypoid bevel gears or any other type of bevel gears. It should also be noted that the second transmission means to be used in the present invention is in no way limited to bevel gears and may be composed of any device that is capable of both changing the rotational direction by 90 degrees or other desired angles and reducing the rotational speed. Thus, the bevel gears as the second transmission means may be replaced by a speed-reducing worm gear, assembly and the like.

The reaction apparatus 10 of the present invention is so designed that as the reaction vessels 50 secured to the peripheral region of the rotating element 12 revolve about the central shaft 14, the sample solution 51 in each reaction vessel moves downward in the direction of gravity and is agitated while being in contact with the inside surface of the reaction vessel, whereby the reaction of interest is promoted. Optimum conditions for promoting the reaction are attained at a point where the difference between the relative speeds of the solid and liquid phases in the reaction vessel 50 that is created by its rotation (one rotation about its own axis per revolution about the central shaft 14, and this rotation is hereinafter referred to as the "revolution") is maximum within the range where the binding between antigen and antibody is not destroyed. Such optimum conditions will vary with the viscosity and surface tension of the sample solution 51, the centrifugal force that is exerted upon it by rotation, and other factors, and may be determined as appropriate depending upon the antigen and antibody which contribute to the reaction of interest, as well as the medium containing either one of these reactive substances.

Figure 5:
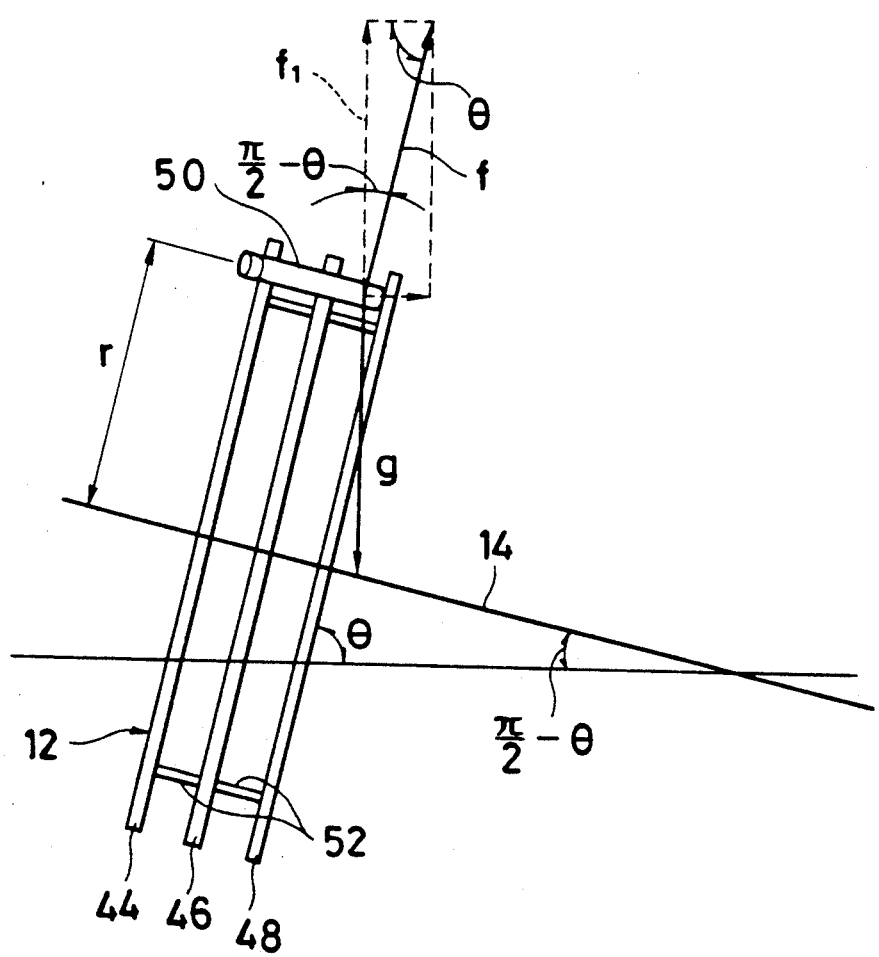
FIG. 5 illustrates an operation of the reaction apparatus shown in FIG. 1.

The practical range over which a desired promotion of the reaction can be attained by the apparatus 10 of the present invention may be defined in terms of centrifugal force as determined by the following parameters: the radius r of the rotating element 12 (to state more exactly, the distance from the central shaft 14 of the rotating element 12 to the center of each reaction vessel 50), the angle of its inclination $\theta$, and the angular velocity of its rotation $\omega$ (see FIG. 5). When the rotating element 12 is rotating about the central shaft 14, the centrifugal force f being exerted upon the sample solution 51 within the reaction vessel 50 is expressed by:

$$ti\ f = mr\omega^2$$

(see FIG. 5)

where m is the mass of the sample solution. The component $f_1$ of the force f which acts in the vertical direction is expressed by:

$$f_1 = mr\omega^2 \sin\theta.$$

If $f_1$ becomes greater than the gravity, mg, of sample solution 51 in the reaction vessel 50, said sample solution will be urged in the direction of centrifugal force and is no longer capable of attaining maximum contact area with the inside surface of the reaction vessel 50, whereupon the efficiency at which the reaction is promoted will decrease.

Hence, the condition for insuring that the apparatus 10 will achieve the intended promotion of the reaction of interest is:

$$f_1 = mr\omega^2 \sin\theta < mg$$

$$f_1/m = r\omega^2 \sin\theta < g.$$

The tilting means for allowing the rotating element 12 to be inclined at the predetermined tilt angle is composed of the frame unit 16 which serves as a member for supporting the aforementioned central shaft 14, and a pivoting means that pivotally supports this frame unit 16 by means of both the drive shaft 22 crossing with the central shaft 14 at a right angle and the pivotal shaft 26 which has a central axis in common with said drive shaft 22 and which is secured to the frame member 16a of the frame unit 16. The pivoting means also pivots the frame unit 16 from its vertical position together with the central shaft 14. The frame members 16a and 16b are parallel to the central shaft 14 whereas the frame members 16c and 16d are vertical to the longitudinal axis of the central shaft 14.

The pivoting means is composed of a first rotational drive source such as motor 36 and a first transmission means which is composed of the toothed pulleys 28 and 30 and the toothed belt 32, but the present invention is not limited to this particular embodiment, and various other pivoting means may be used to perform the necessary rotational control as long as they are capable of controlling the rotational angles in an exact manner.

In the example shown, the toothed pulley 28 is secured to the pivotal shaft 26 whereas the other toothed pulley 30 is secured to the drive shaft 34 which in turn is joint-coupled to the motor 36. The toothed belt 32 is stretched between these toothed pulleys 28 and 30. By means of these elements, the rotation of the drive shaft 34 is transmitted to the pivotal shaft 26 so that the frame unit 16 is pivoted by a predetermined angle to tilt the central shaft 14, whereby the rotating element 12 can be inclined by a predetermined angle from the horizontal position. For the purposes of the present invention, the tilt angle or the angle of inclination, $\theta$, of the rotating element 12 may be such that the sample solution in any reaction vessel 50 will not be spilled but maximizes the contact area of the sample solution 51 with the inside surface of that vessel. A useful range of $\theta$ is from 10 to 88 degrees and the range of 60 to 85 degrees is most preferred. The angle of inclination $\theta$ may be either fixed or adjustable in accordance with the type of a specific reaction vessel used.

The first transmission means may be of any type as long as the rotation of the drive shaft 34 by means of the motor 36 can be transmitted correctly to the pivotal shaft 26. Illustrative examples of such first transmission means include gears, belts and chains.

The motor 36 may be of any type that is capable of allowing the rotating element 12 to pivot between the horizontal position and the inclined position where it is inclined at a predetermined angle. Preferred examples include a stepping motor capable of stepwise rotation in either a forward or a reverse direction, AC and DC servo motor, ultrasonic motor and the like.

The drive shafts 22 and the motor 24 are respectively provided with the sensors 38 and 25, which detect the position of the seat in the rotating element 12. The driving shaft 34 and the motor 36 are respectively provided with the sensors 40 and 37, which detect whether the rotating element 12 is in the horizontal or in the inclined position. The sensor 38 (or 40) comprises a thin disk 38a (or 40a) with a partial cutout or a notch that is secured to the drive shaft 22 (or 34) and a photodetector 38b (or 40b) composed of a light-emitting and a light-receiving element. The sensors 25 and 37 also have a similar construction, and are respectively mounted to the motors 24 and 36 to their rotational shafts. The sensor 25 (or 37) comprises a thin disk 25a (37a) with a notch and a photodetector 25b (or 37b). In sensors 25 (37, 38 or 40), when the light beam issuing from the light-emitting element is blocked by the disk 25a (37a, 38a or 40a), it cannot be admitted by the light-receiving element. On the other hand, if that beam is incident on the cutout in the disk 25a (37a, 38a or 40a), it is admitted by the light-receiving element and the detected optical output can be used as a sync signal for detecting the rotational or tilt position of the rotating element 12. Alternatively, the sensor 25 and 37 may be replaced with rotary encoders for the purpose of accurate control.

The sync signal to be obtained may be of any pattern. For example, the sensor 38 may be used to detect the initial position of the rotating element 12 in the horizontal state, and the sensor 40 may be used to detect whether the rotational element 12 is in its horizontal or inclined position.

The sensor 25 is employed in addition to the sensor 38 to improve the detection accuracy of the rotating element 12 to a level higher than that achieved by the sensor 38 alone. Since the sensor 38 is mounted on the rotating shaft 22, which is in turn connected to the rotating shaft of the motor 24 via a reduction gear 72, the sync signal obtained by the sensor 25 of the motor 24 would be more accurate than the sync signal obtained by, the sensor 38 to a degree proportional to the reduction ratio of the reduction gear 72. The sensor 37 is employed for a similar purpose as the sensor 25. Since the sensor 40 is mounted on the rotating shaft 34 which is in turn connected the rotating shaft of the motor 36 via a reduction gear 66, the sync signal obtained by the sensor 37 would be more accurate than the sync signal obtained by the sensor 40 to a degree proportional to the reduction ratio of the reduction gear 66.

Needless to say, the control over the rotation and tilting of the rotating element 12 may be entirely effected with the sensors 38 and 40. In this case, rotary encoders may preferably be mounted on the motors 24 and 36, respectively instead of employing the sensors 25 and 37 to control the rotation (particularly its flutters) of the respective motors 24 and 36. Alternatively, the sensors 38 and 40 may respectively be combined with the rotary encoders mounted on the motors 24 and 36, respectively, to perform the necessary control.

The sensors 25, 37, 38 and 40 are in no way limited so long as the angle or the number of the rotation is detected. Rotary encoders and any other sensor known to the art may be employed.

The sensors 25, 37, 38 and 40, and motors 24 and 36 are connected to the control unit 42. In response to the sync signals from the sensors 25, 37, 38 and 40, the control unit 42 controls the motors 24 and 36 in such a way that the rotating element 12 will pass through a predetermined number of cycles each consisting of the following steps in sequence, i.e., stop in the horizontal state, tilting, rotation at a constant speed for a predetermined time at the tilted state, stop of the rotation, return to the horizontal state, stop in the horizontal state and rotation by a predetermined angle. If the rotating element 12 has 62 seats for the reaction vessels 50 as in the case under discussion, at least 62 cycles of these steps must be repeated. The motors 24 and 36 are connected to a power source not shown.

In the reaction apparatus of the present invention, the motor 36 is mounted on a support plate 65 secured vertically to a platform 64, and is coupled to the drive shaft 34 via a reduction gear 66 and a shaft coupling 67. The drive shaft 34 is supported on both ends by bearings 68 that are secured to the platform 64. The disk 40a of the sensor 40 is mounted intermediate between the opposite ends of the drive shaft 34, with the photodetector 40b being mounted on the platform 64 in such a way that the peripheral edge of the disk 40a is placed between the associated light-emitting and light-receiving elements of the sensor 40.

The motor 24 is mounted on a support plate 71 secured vertically to a table 70 and is coupled to the drive shaft 22 via a reduction gear 72 and a shaft coupling 73. The drive shaft 22 is supported on both ends by the bearings 68 which are also secured to the table 70. The disk 38a of the sensor 38 is mounted intermediate between the opposite ends of the drive shaft 22, with the photodetector 38b being mounted on the table 70 in such a way that the peripheral edge of the disk 38a is placed between the associated light-emitting and light-receiving elements. The table 70 is secured to the platform 64 by means of four struts 74.

The pivotal shaft 26 secured to the frame unit 16 is supported by the bearing 68 on a small table 76 in such a way that it is in conformity with the drive shaft 22 as regards the central axis. The small table 76 is secured to the platform 64 by two struts 74 in such a way that it is equal in height to the table 70.

Further in order to carry out the intended reaction at a predetermined temperature in the apparatus 10 of the present invention, at least the rotating element 12 is preferably accommodated within a thermostatic chamber or incubator 78. In the example shown in FIG. 1, all parts of the reaction apparatus except the control unit 42 are accommodated in the thermostatic chamber 78 but the present invention is in no way limited to this particular case alone. The thermostatic chamber or incubator 78 is enclosed with a highly heat-insulating case 79. In order to maintain the temperature in the chamber 78 at a desired constant level within the range of, for example, 15°-40° C., a known thermostatic device 80 is preferably provided within the chamber or incubator 78. Thus, the temperature in the thermostatic chamber 78 is held at a uniform level while the sample solution 51 in each of the reaction vessels 50 is agitated by whirling them to carry out the reaction with the reactive substance immobilized on the inside surface of each vessel and, as a results, the reaction temperature can be made uniform enough to insure that the reaction is carried out under the same conditions for all reaction vessels 50 used.

Having described above the basic features of the non-limiting construction of the apparatus of the present invention for carrying out the reaction between a solid and a liquid phase, we now describe the operational aspects of this apparatus. The following description is based on FIGS. 4a–4f and is directed to the operation of the reaction apparatus 10 shown in FIGS. 1–3.

Prior to the start of operation, the rotating element 12 is in a horizontal position as shown in FIGS. 1 and 2. As shown in FIG. 4a, a seat with number A1 (hole 56) for holding a reaction vessel 50 is located at station S1, and a seat with number A23 is located at station S23. In the example shown, the rotating element 12 has 62 seats which are identified by sequential numbers assigned to the holes 56 counterclockwise. It is also assumed here that reaction vessels 50 are not placed in all the seats present. Pinchers 58 and 60 are provided at station S1 whereas pincher 62 is provided at station S23.

In the first cycle of operations, the rotating element 12 rests in a horizontal state and a reaction vessel 50 containing a sample solution 51 is transferred from an automatic sampler or some other suitable device and is set in seat A1 at station S1 by means of pincher 58.

Thereafter, the control unit 42 is actuated to drive the motor 36 and rotate the drive shaft 34 in a predetermined amount, where upon the toothed pulley 28 is rotated by means of the toothed belt 32 stretched between said pulley 28 and the other toothed pulley 30. The rotating pulley 28 causes the pivotal shaft 26 to rotate by a predetermined angle, say, 80 degrees, so that the central shaft 14 is inclined from the vertical position by the same angle until the rotating element 12 tilts by an angle of 80 degrees with respect to the horizontal plane. Thereafter, the motor 36 is brought to a stop so that the rotating element 12 will rest in the inclined state.

With the rotating element 12 being inclined, the control unit 42 drives the motor 24 which in turn drives bevel gears 18 and 20 so that the rotating element 12 is rotated continuously around the central shaft 12 at a constant speed (e.g. 30 rpm) for a predetermined time (e.g. 25 seconds). After the lapse of the predetermined time (25 seconds), the motor 24 is brought to a stop so that the rotating element 12 will no longer rotate in the inclined state. Then, the motor 36 is allowed to rotate in a reverse direction until the rotating element 12 in the inclined position returns to the initial horizontal position. The motor 36 is then brought to stop and remains at rest for a short time. Thereafter, the motor 24 is driven to rotate the rotating element 12 clockwise (in the direction of arrow B) by an angle equivalent to one pitch (5.81 degrees if there are 62 seats available), whereupon the operation proceeds to the second cycle shown in FIG. 4b.

As in the first cycle described above, the second cycle consists of the steps of allowing the rotating element 12 to rest in its horizontal state for the removal of the reaction vessel, tilting the rotating element, rotating the element in an inclined state, stopping the rotation of the rotating element in its inclined state, bringing the element back to the horizontal state, allowing the element to rest in the horizontal state for the insertion of the reaction vessel, and rotating the element by one pitch. Thus, the rotating element 12 is allowed to rotate successively by one pitch in the direction of arrow B.

In the example described above, each cycle requires 30 seconds to complete and a total of 5 seconds is spent by the steps of allowing the rotating element 12 to rest in a horizontal state, tilting it, bringing it back to the horizontal state and allowing it to rest in the horizontal state.

Figure 4C:
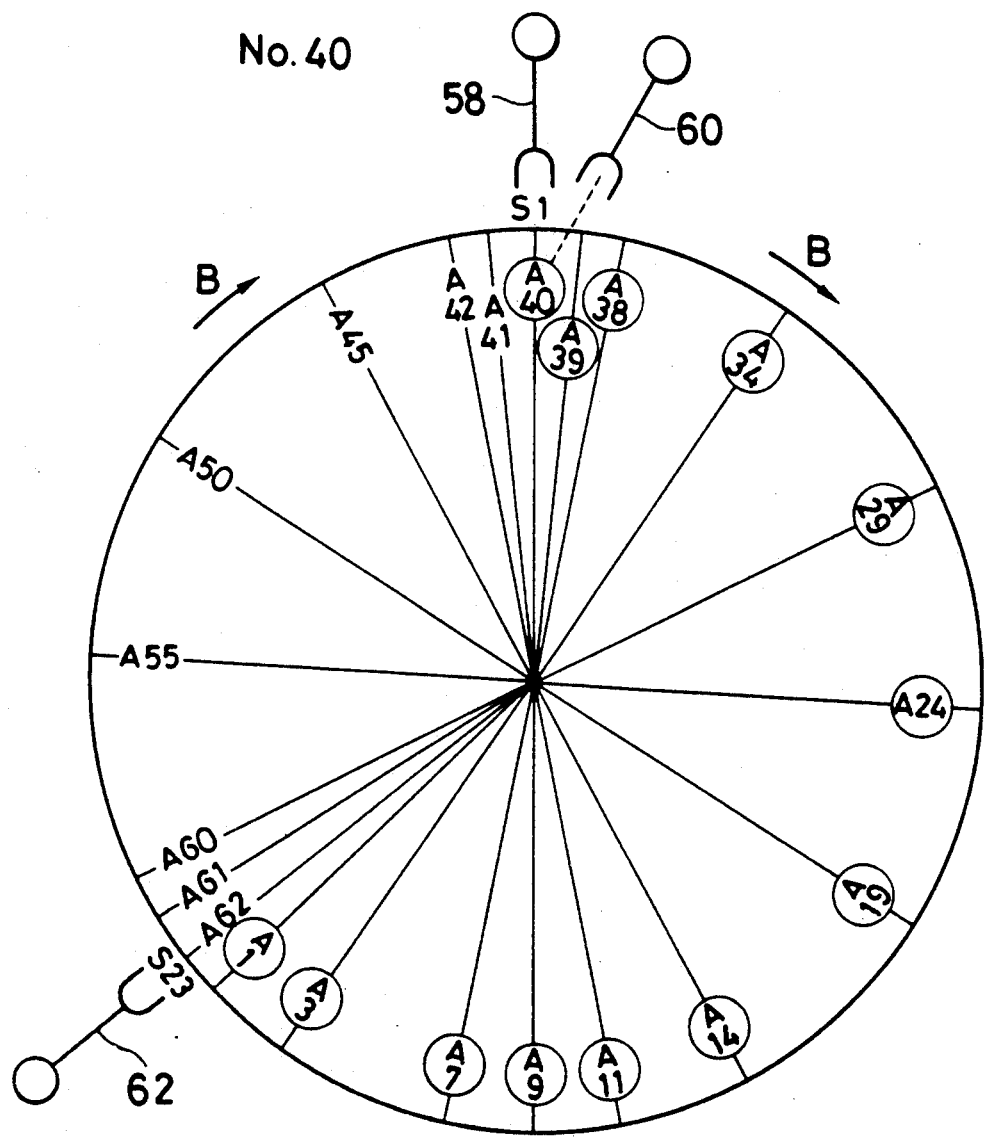
Figure 4D:
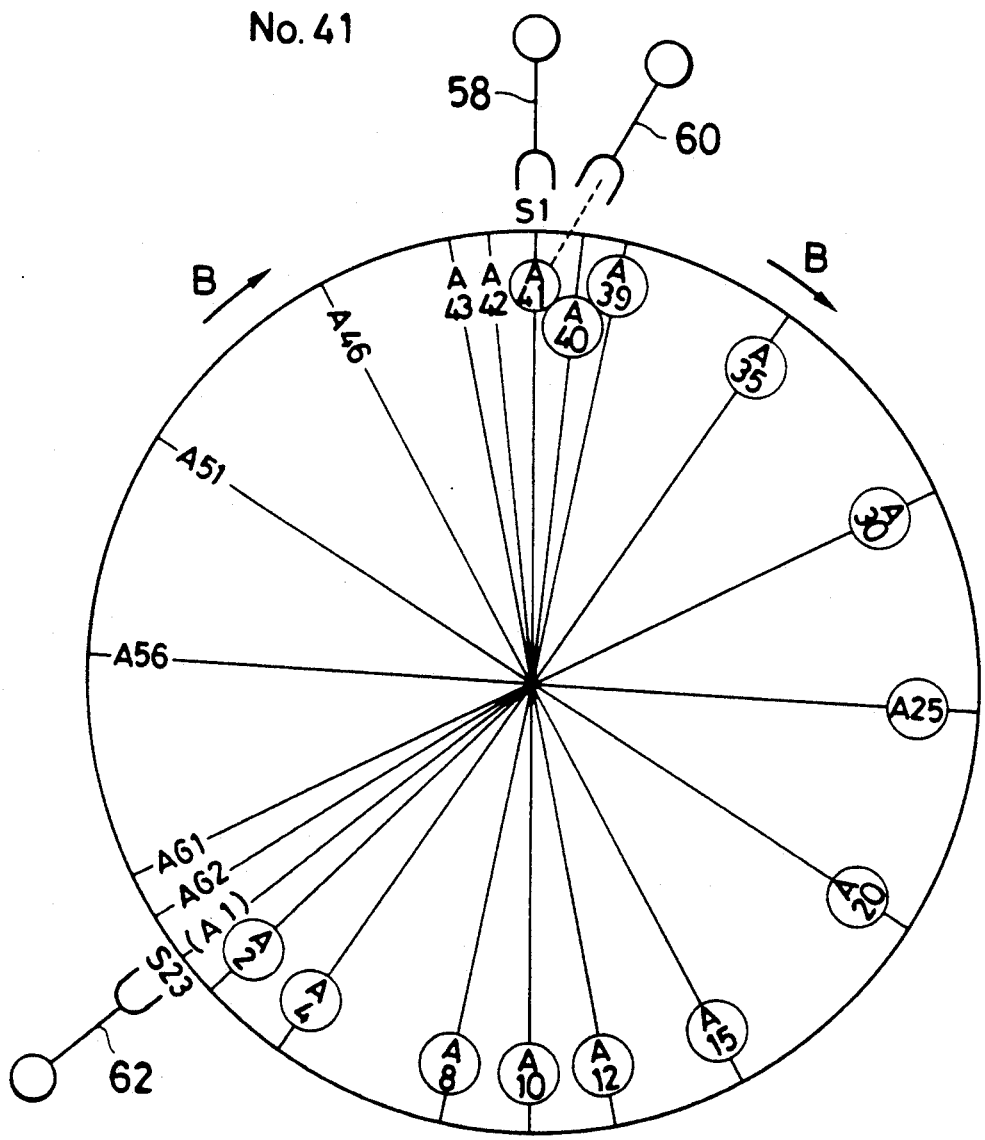
Figure 4E:
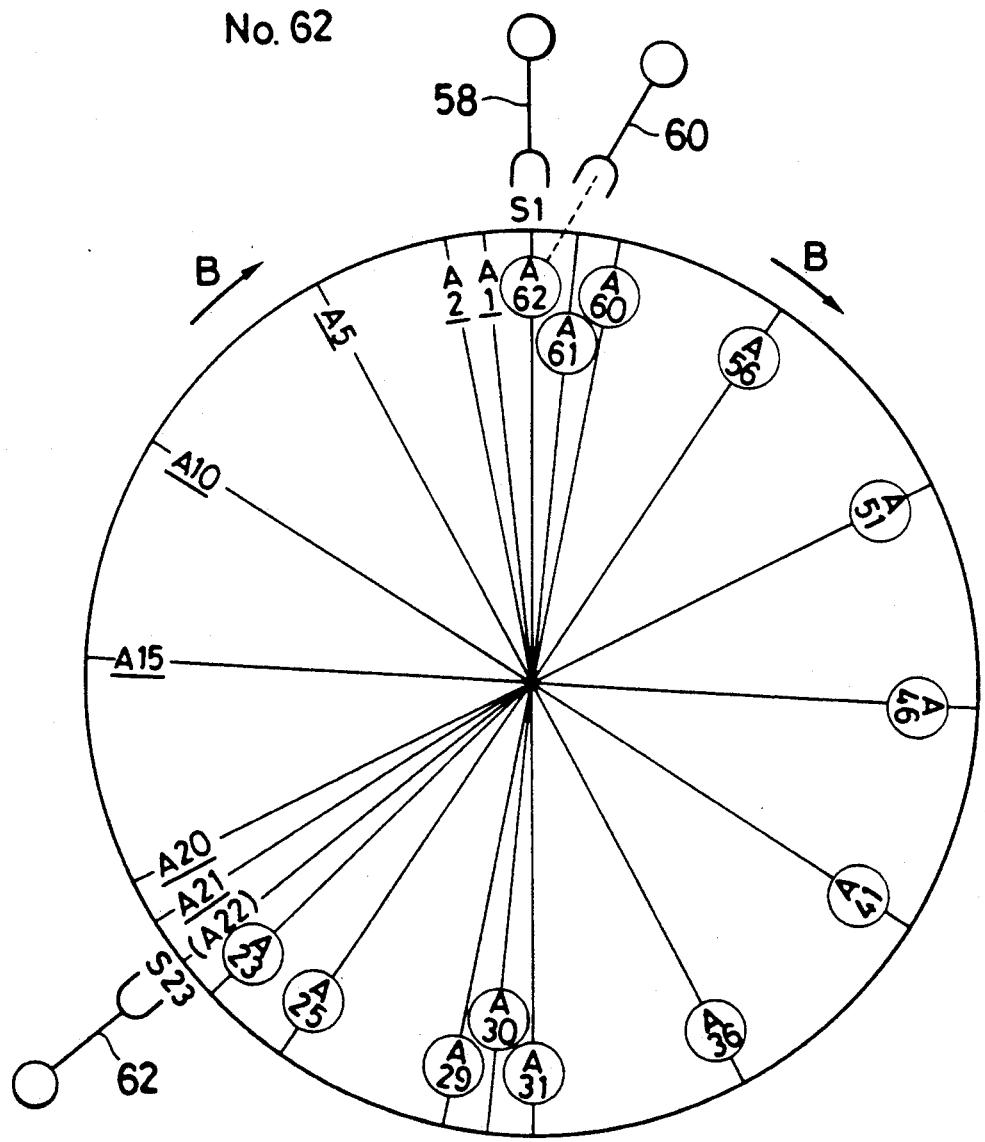

The same procedure is repeated up to the 40th cycle. As shown in FIG. 4c, however, station S23 is not occupied by the reaction vessel 50 up to the 40th cycle, so that pincher 62 does not work to unload any reaction vessel 50. Needless to say, reaction vessels 50 are also absent from station S1 after the rotating element 12 is rotated by one pitch in the horizontal position, so pincher 60 also does not work to unload any reaction vessel.

In the next cycle (41st cycle), seat A1 where the reaction vessel 50 is present comes to station S23 (see FIG. 4d), and the pincher 62 will move horizontally and vertically in the first rest period to unload the reaction vessel 50 from seat A1 in the rotating element 12 so that it can be subjected to necessary posttreatments.

Since the sample solution 51 in the removed reaction vessel 50 has passed through 40 cycles, the overall reaction time is exactly 20 minutes assuming that one cycle is completed in 30 seconds.

The reaction vessel 50 thus removed is set in a cleaner, washed, set under a substrate-injection nozzle, and injected with the substrate for enzyme reaction.

After the removal of the reaction vessel 50, the rotating element 12 will rotate in its inclined state, stop its rotation in the inclined state, and then return to its initial horizontal position in accordance with the aforementioned cycles of steps, and, while it is at rest in the horizontal position, the pincher 62 will reload the treated reaction vessel 50 in seat A1 at station S23.

The above-described cycles are repeated. Up to the 62nd cycle shown in FIG. 4e, however, no reaction vessel 50 is present at station S1 and, hence, the pincher 60 will not work to unload reaction vessels 50. Needless to say, the pincher 58 at station S1 continues the loading operation whereas the pincher 62 at station S23 continues the loading/unloading operations.

Figure 4F:
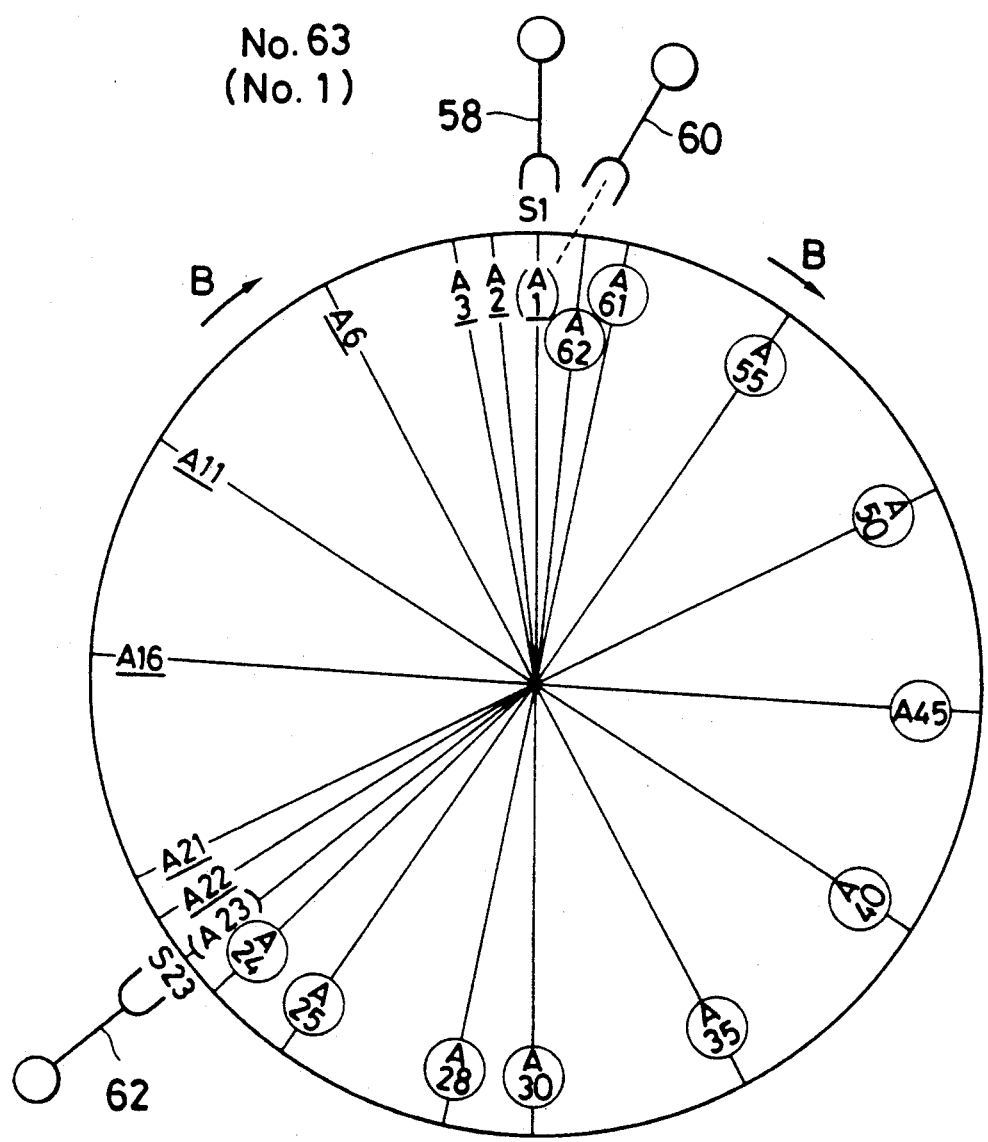

In the 63rd cycle shown in FIG. 4f, the reaction vessel 50 is already present in seat A1 at station S1 because seat A1 has been rotated by one pitch to arrive at station S1, so that the pincher 60 will remove the reaction vessel 50 by pinching. At the same time, the pincher 62 will remove the reaction vessel 50 from seat A23 at station S23. When the rotating element 12 returns to its initial horizontal position after rotating in its inclined state the pincher 58 will set in vacant seat A1 a unused reaction vessel 50 which has not been subjected to any reaction. At the same time the pincher 62 at station S23 will reset the washed reaction vessel 50 to which the substrate has been injected in seat A23 and the rotating element 12 will rotate by one pitch.

Since the reaction vessel 50 removed with the pincher 60 has been subjected to 21 repetitive cycles, the reaction time may be calculated as 10 minutes and 30 seconds assuming that one cycle takes 30 seconds for completion.

After being removed from the rotating element 12, the reaction vessel 50 in which the reaction with the substrate continued for a predetermined time is set in a stopping reagent injecting nozzle, injected with a stopping reagent, set in an agitator and stirred. Thereafter, the vessel is set at the entrance to an photometer, set in the measuring position and subjected to an absorbance measurement. Subsequently, the vessel is returned to the entrance to the photometer by means of an air lift, a mechanical lift or some other suitable lift mechanism, and set in a drain nozzle, where the liquid content of the vessel is drawn off by suction and discarded.

As described above, the apparatus of the present invention insures that an antigen-antibody reaction and subsequent reactions with the substrate can be correctly carried out within a short period of time using a simple mechanism and yet the reaction time is uniform and precise for all samples involved.

On the foregoing pages, there has been described the first aspect of the present invention which is directed to an apparatus for promoting the reaction between a solid and a liquid phase wherein the rotating element is allowed to rotate in an inclined state with reference to the second aspect of the present invention, in which reaction vessels are loaded and unloaded from the rotating element in its horizontal state. It should, however, be noted that the present invention is in no way limited to this particular embodiment and that reaction vessels may be loaded and unloaded with the rotating element being in an inclined state. An example of the reaction apparatus of this type is described below with reference to FIGS. 6 and 7.

The reaction apparatus generally indicated by 100 comprises:

a rotating element 104 which is mounted in a way freely rotatable about a longitudinal axis 102 inclined with respect to the horizontal direction;

a rotational drive means 106 which allows said rotating element 104 to rotate about the axis 102;

a reaction vessel securing means 110 provided in the peripheral region of said rotating element 104 in such a way that a tubular reaction vessel 108 containing a liquid phase to react with a solid phase bound to its inside surface can be detachably secured to said rotating element 104; and a reaction vessel loading/unloading device 126 that comprises a lower arm 114 which moves either above or below the position where said reaction vessel 108 is secured with said reaction vessel securing means 110 by pivoting about a shaft 112 provided above said rotating element 104 to cross said longitudinal axis 102 at a right angle, a first eccentric cam 116 for causing said lower arm 114 to pivot, a first drive source 118 for causing said first eccentric cam 116 to rotate, an upper arm 120 which pivots about a shaft 112 common to said lower arm 114 in such a way that the reaction vessel 108 is held between said lower arm 114 and said upper arm 120, a second eccentric cam 122 for causing said upper arm 120 to pivot, and a second drive source 124 for causing said second eccentric cam 122 to rotate, which upper arm 120 and lower arm 114 holding said reaction vessel 108 therebetween are allowed to pivot by the rotation of said first eccentric cam 116 and second eccentric cam 122 in a predetermined direction so that said reaction vessel 108 engages said reaction vessel securing means 110 whereas the upper arm 120 and lower arm 114 are allowed to pivot by the rotation of said first and second eccentric cam 116 and 122 in reverse direction so that said reaction vessel 108 is held between said two arms to be disengaged from said reaction vessel securing means 110.

When the rotating element having said reaction vessel secured to its peripheral region by the vessel securing means is allowed to rotate about the longitudinal shaft which is inclined by a predetermined angle with respect to the horizontal direction, the reaction vessel will also revolve about said longitudinal shaft. The reaction vessel will make one rotation about its own axis in the direction of gravity while the rotating element rotates fully once, whereby the sample solution in the reaction vessel is moved around the inside surface to attain maximum contact of the surface area.

Thus, by insuring that the rotating element is rotated in a correct way, the reaction vessel can also be made to rotate correctly without any slippage or erratic rotation, so that even if a plurality of reaction vessels are used simultaneously, the solid and liquid phases in each reaction vessel are permitted to react with each other under entirely the same conditions with respect to rotation and mixing.

Figure 6:
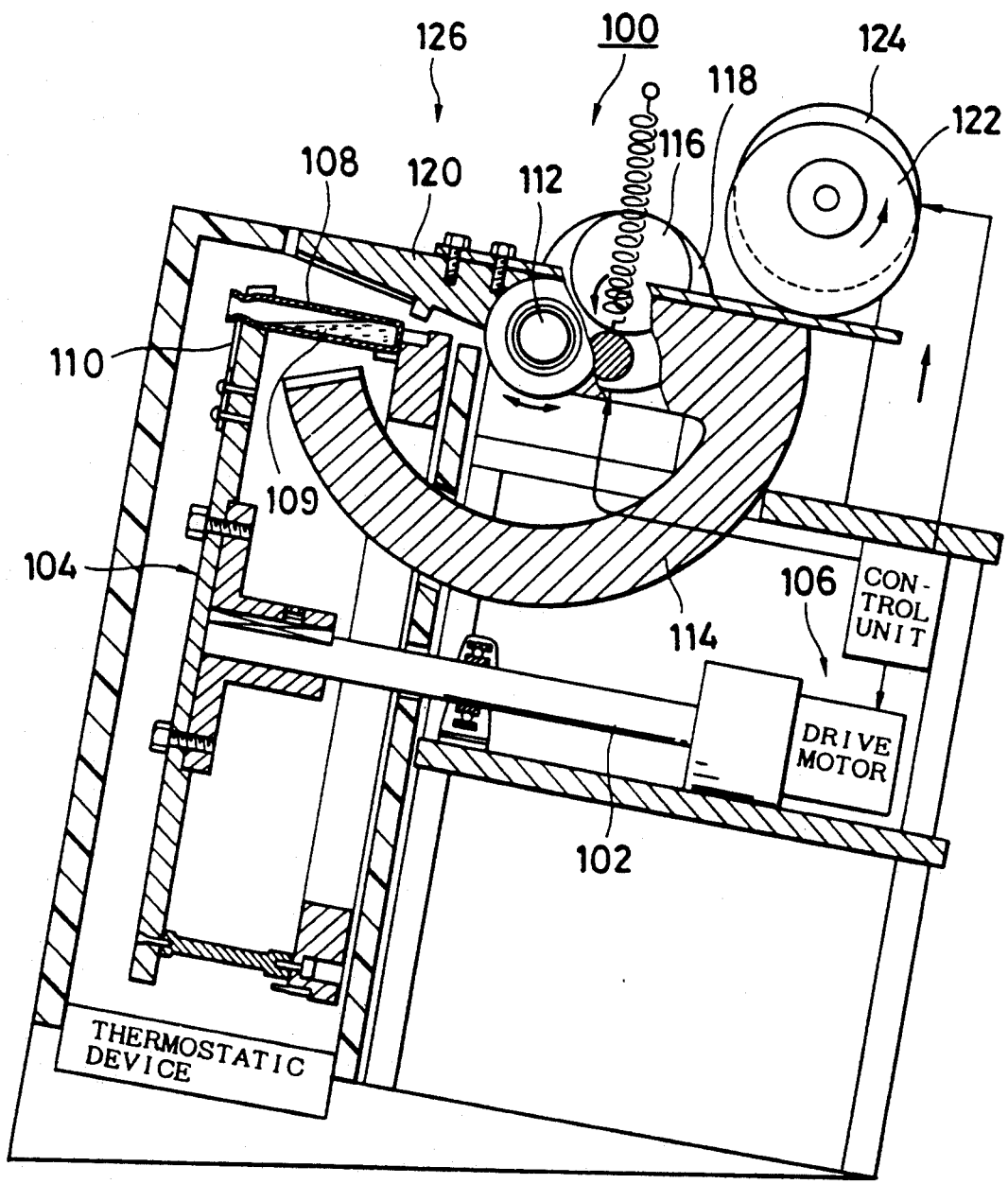
FIGS. 6 and 7 are a cross-sectional side view and a partial enlarged perspective view, respectively, of another example of the apparatus of the present invention for carrying out the reaction between a solid and a liquid phase.
Figure 7:
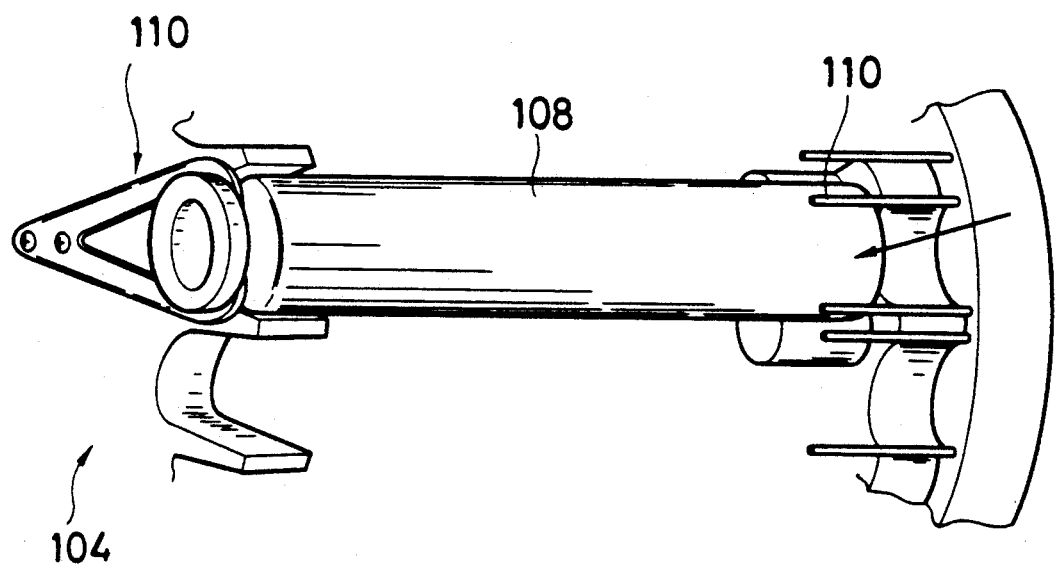

Assume here that the reaction apparatus 100 shown in FIG. 6 has more than one, say, sixty, reaction vessel securing means 110 that are provided equidistantly on the same circumference in the peripheral region of the rotating element 104. When reaction vessels 108 are loaded on the rotating element 104, the latter will start to rotate at a predetermined speed for a predetermined time, whereupon the individual reaction vessels 108 revolve around the longitudinal shaft 102 as they are secured to the periphery of the rotating element 104. To state more specifically, when the rotating element 104 rotates fully once, each reaction vessel 108 will make one revolution in the direction of gravity, with its longitudinal axis remaining inclined by a predetermined angle, say, 10 degrees, with respect to the horizontal plane. Accordingly, the sample solution 109 accommodated within each reaction vessel 108 will move around the inside surface to attain maximum contact of the surface area so as to react with an antibody or an other reactive substance that is bound to the inside surface of said reaction vessel.

After the rotating element 104 has been allowed to rotate for a predetermined time, it is brought to a stop and again rotated in such a way that the position where a reaction vessel 108 of interest is loaded, say, the topmost position of the rotating element 104 goes down by a certain pitch (i.e. 360/n in degrees where n is the number of reaction vessels 108 loaded on the rotating element 104; if n is 60, one pitch will be 6 degrees) and the adjacent position will become the highest, where a reaction vessel is to be loaded or unloaded from the rotating element 104. When this new topmost position is reached, the rotating element 104 is allowed to stop rotating. If a reaction vessel 108 is in that position, it is removed by the sequence of steps which is reverse to that for the loading operation. If there is no reaction vessel in that position, the reaction vessel loading/unloading device 126 is used to load an unused reaction vessel 108.

After the unused reaction vessel is loaded, the rotating element 104 is allowed to rotate for a predetermined time in the manner described above and the following sequence of steps is thereafter repeated: bringing the rotating element to a stop in the position which advances by 6 degrees; loading an unused reaction vessel 108 if there is none in that advanced position (unload if any); and allowing said element to rotate for a predetermined time.

In the manner described above, the sequence of steps including unloading, rotation, stopping, loading, advancing 6 degrees and next unloading, are repeated 60 times until the initial position of the rotating element 104 comes to the position where the reaction vessel is to be loaded or unloaded. Since the initially loaded reaction vessel 108 is in that position, said vessel is unloaded by means of the device 126, brought to an upright position and fed to the next operational step.

When the plurality of reaction vessels 108 are loaded on the reaction apparatus 100 and whirled to effect mixing in the manner described above, none of them will experience any slippage and, instead, the contents of each reaction vessel are mixed by rotation that is performed for a predetermined time in a predetermined number of revolutions, whereby the intended reaction can be carried out under completely identical conditions in all reaction vessels.

The time and the number of revolutions (rotational speed) which are associated with the continuous rotation of the rotating element 104 that is defined by the "start of rotation" and terminated by "6-degree advancement until stopped" may be determined as appropriate in accordance with the overall time of whirl mixing, namely, the intended reaction time. Fore example, if the total reaction time, the time necessary to load and unload reaction vessels and the number of reaction vessels 50 used are written as T (min), t (min) and n, respectively, the time of a single continuous rotation may be determined by $(T/n)-t$ (min).

Thus, in accordance with the present invention, reaction vessels 108 can be automatically mounted and dismounted from the reaction vessel securing means 110 and this enables a reaction of interest to be carried out uniformly in the reaction vessels 108, thereby contributing to the realization of automated measurements.

The procedures of loading and unloading reaction vessels with the reaction vessel loading/unloading device used in the present invention may be summarized as follows. In the loading mode, a tubular reaction vessel that is open at one end and which accommodates a liquid phase to react with a solid phase bound to its inside surface is held, with the open end facing up, between the upper and lower arms under the action of the first eccentric cam which rotates in a predetermined direction, and is moved to the associated loading position in the reaction apparatus which is inclined by predetermined angle with respect to the horizontal direction; then, under the action of the first and second eccentric cams, said reaction vessel is loaded in said loading position in a reliable and correct way by means of said upper and lower arms. When the first and second eccentric cams are rotated further, the upper and lower arms are disengaged from the reaction vessel, with the reaction vessel being loaded on the rotating element. The rotating element is then rotated for a predetermined time to complete a predetermined number of rotations to insure that the solid and liquid phases in the vessel will thoroughly react with each other. Thereafter, the rotation of the reaction vessel is stopped and it is unloaded from the loading position by being held between the upper and lower arms under the action of the first and second eccentric cams which rotate in a reverse direction.

Because of this mechanical feature, the apparatus of the present invention offers an outstanding advantage in immunoassay procedures that the reaction vessel can be loaded in and unloaded from the loading position in a safe, correct and reliable manner for the rotation of the vessel in an inclined state.

In accordance with the present invention, two eccentric cams are used in loading or unloading the reaction vessel. Stated more specifically, the reaction vessel is loaded in the associated loading position by being held between the upper and lower arms under the action of the first and second eccentric cams. This insures that the reaction vessel can be loaded in the associated loading position without breaking or causing spillage of the liquid content even if a securing means of an elastic or otherwise structure is provided in said loading position or if a drive source for loading such as a motor overruns.

Further, in accordance with the present invention, the reaction vessel is mounted or dismounted from the reaction vessel securing means with the aid of the already described loading/unloading device, and this insures that the reaction vessel can be loaded or unloaded in a simple, reliable and yet smooth way. At the same time, if a proper control means is used, the operations of loading and unloading the reaction vessel can be automatically performed in operative association with the rotational movement of the rotating element and this will eventually lead to the performance of reaction and, hence, measurement procedures in an automated fashion.

A further advantage of the reaction apparatus of the present invention is that, in whichever embodiment, it can be readily equipped with an photometer which measures the absorbance of a sample solution after a substrate reaction for determining the degree of reaction. Hence, the apparatus of the present invention has the potential to perform immunoassays involving immunological, enzymatic and other reactions in a fully automated manner.

As described above in detail, the apparatus of the present invention for carrying out the reaction between a solid and a liquid phase permits a reaction vessel to revolve around the axis of the rotating element which is held in the peripheral region with the reaction vessels and the efficiency with which the reaction of interest can be promoted is by no means lower than that achieved by the prior art versions which must cause the reaction vessel to rotate around its own axis to perform the reaction between the solid and liquid phases. Further, the apparatus of the present invention has no need to allow an individual reaction vessel to rotate around its own axis with the aid of a separately provided rotating means and the intended result can be attained merely by loading the reaction vessel on the rotating element. Because of these features, the apparatus of the present invention has a simple construction resulting in less frequent troubles, can be manufactured at a considerably reduced cost and will hence find extensive use in various applications. In addition, the apparatus of the present invention can be used to perform a reaction of interest successively in a plurality of reaction vessels without causing any slippage or other deleterious effects in the rotation of these vessels and, accordingly, the conditions of rotation and, hence, the reaction of interest can be rendered uniform in all the reaction vessels used.

A particular advantage of the second embodiment of the present invention is that a reaction vessel can be loaded in or unloaded from the reaction apparatus in a horizontal position and that the rotation can be carried out in an inclined state. Therefore, the intended promotion of the reaction can be satisfactorily achieved despite the great ease with which the reaction vessel can be loaded.

Further, the apparatus of the present invention can be applied with advantage to automate the performance of reactions and, hence, measurements.

In the foregoing, the reaction apparatus of the present invention has been described with reference to the first and second aspects of the invention. It is clearly to be understood that the present invention is by no means limited to these embodiments, and may be modified and varied without deviating from the claimed scope of the invention with regard to its various parameters including direction of the rotation of the rotating element, number of the seat provided on the rotating means for holding the reaction vessel, position of the station at which the reaction vessel is set and removed, and the like.

What is claimed is:

1. An apparatus for promoting a reaction in at least one tubular reaction vessel having a longitudinal axis and an inner surface wherein said reaction is promoted between a solid phase immobilized on said inner surface of the reaction vessel and a liquid phase accommodated in the reaction vessel so as to ensure sufficient contact between said solid phase and said liquid phase through rotation of the reaction vessel which is held at a predetermined tilt angle, said tilt angle being determined such that the liquid phase becomes substantially in full contact with the inner surface of the reaction vessel without spilling out of the reaction vessel, said apparatus comprising:

a rotating element which is fixedly secured to a central shaft, said central shaft being positioned substantially perpendicular to said rotating element, said central shaft extending in a direction substantially parallel to the longitudinal axis of a reaction vessel, drive means for rotationally driving said rotating element, means for holding the tubular reaction vessel in a peripheral region of said rotating element, tilting means for tilting said rotating element at a predetermined tilt angle while still allowing said central shaft to extend in a direction substantially parallel to the longitudinal axis of the reaction vessel, and control means for controlling said drive means and said tilting means to allow said rotating element to undergo a predetermined number of cycles which each comprise standing for a predetermined period of time in a horizontal position, tilting to said predetermined tilt angle, rotating while in the tilted state at a predetermined substantially constant speed for a predetermined period of time, returning to the horizontal position, standing for a predetermined period of time in the horizontal position, and rotating a predetermined angle while in the horizontal position.

2. An apparatus according to claim 1 wherein said rotating element comprises a top disk, one or more intermediate disks and a bottom disk which are aligned in interspaced relationship and secured to one another, said central shaft being secured to at least one of said disks; and wherein said holding means comprises a predetermined number of through holes into which said reaction vessel can be inserted and said bottom disk which supports said reaction vessel at its bottom, said through holes being positioned in said top disk and all of said intermediate disks within peripheral regions of the respective disks so that the holes in each disk are concentrically positioned around said central shaft while holes of adjacent disks are aligned parallel to said central shaft.

3. An apparatus according to claim 1 wherein said tilting means comprises a support member for rotatably supporting said central shaft, a pivotal shaft that is secured to said support member and which crosses said central shaft at a right angle, and a pivoting means which causes said rotating element to tilt by pivoting said pivotal shaft by said predetermined tilt angle.

4. An apparatus according to claim 3 wherein said pivoting means comprises a first rotational drive source and a first transmission means.

5. An apparatus according to claim 4 wherein said first transmission means comprises a toothed pulley mounted on said pivotal shaft, another toothed pulley mounted on a drive shaft coupled to said first rotational drive source, and a toothed belt stretched between said toothed pulleys.

6. An apparatus according to any one of claims 2 to 5 and 1 wherein said rotational drive means comprises a second rotational drive source and a second transmission means.

7. An apparatus according to claim 6 wherein said second transmission means comprises a bevel first gear mounted on said central shaft and another bevel gear that meshes with said first bevel gear and which is mounted on the drive shaft coupled to said second rotational drive source.

8. An apparatus according to claim 1 wherein said predetermined tilt angle is in the range of from 60 to 85 degrees.

9. An apparatus according to any one of claims 3 to 5 wherein said support member comprises a rectangular frame unit comprising four frame members, said four frame members defining first and second pairs of parallel frame members, said central shaft of the rotating element being supported by said first pair of parallel frame members of said frame unit, said pivotal shaft being secured to one of the frame members of said second pair of frame members, and said rotational drive means comprising a second rotational drive source coupled to a second drive shaft, said second drive shaft being supported on the other side of the frame members of said second pair of frame members, a first bevel gear mounted on said central shaft within said frame unit, and a second bevel gear mounted on said second drive shaft, said second bevel gear meshing with said first bevel gear.

10. An apparatus according to claim 1 further comprising an incubator wherein said rotating element is accommodated within said incubator.

11. An apparatus according to claim 1, wherein said control means controls said drive means and said tilting means so that promotion of the reaction in the reaction vessel is carried out by rotation of said rotating element in the tilted state at the predetermined substantially constant speed for the predetermined period of time.

12. An apparatus according to claim 1, wherein said holding means is constructed to hold said reaction vessel in a substantially stationary state during rotation of the rotating element.

* * * * *